US00PP19186P2

(12) United States Plant Patent
Dümmen

(10) Patent No.: US PP19,186 P2
(45) Date of Patent: Sep. 9, 2008

(54) ***GERANIUM* PLANT NAMED 'DUEPAIMVIO'**

(50) Latin Name: *Pelargonium peltatum*
Varietal Denomination: Duepaimvio

(75) Inventor: Tobias Dümmen, Rheinberg (DE)

(73) Assignee: Capitol Green Investments Ltd., Grand Cayman (KY)

( * ) Notice: Subject to any disclaimer, the term of this patent is extended or adjusted under 35 U.S.C. 154(b) by 0 days.

(21) Appl. No.: 11/804,342

(22) Filed: May 17, 2007

(51) Int. Cl.
*A01H 5/00* (2006.01)

(52) U.S. Cl. ..... Plt./332
(58) Field of Classification Search ..... Plt./332
See application file for complete search history.

*Primary Examiner*—Anne Marie Grunberg
*Assistant Examiner*—Louanne C Krawczewicz Myers
(74) *Attorney, Agent, or Firm*—C. A. Whealy

(57) ABSTRACT

A new and distinct cultivar of Ivy *Geranium* plant named 'Duepaimvio', characterized by its compact and outwardly spreading plant habit; freely basal branching habit; freely flowering habit; double red purple-colored flowers; and good garden performance.

1 Drawing Sheet

Botanical designation: *Pelargonium peltatum.*
Cultivar denomination: 'DUEPAIMVIO'.

BACKGROUND OF THE INVENTION

The present invention relates to a new and distinct cultivar of Ivy *Geranium*, botanically known as *Pelargonium peltatum,* and hereinafter referred to by the name 'Duepaimvio'.

The new Ivy *Geranium* is a product of a planned breeding program conducted by the Inventor in Rheinberg, Germany. The objective of the breeding program is to create new uniform Ivy *Geranium* cultivars with numerous and attractive flowers.

The new Ivy *Geranium* originated from a cross-pollination made by the Inventor in August, 2002 in Rheinberg, Germany of a proprietary selection of *Pelargonium peltatum* identified as code number S-01-06, not patented, as the female, or seed, parent with a proprietary selection of *Pelargonium peltatum* identified as code number E-01-02, not patented, as the male, or pollen, parent. The cultivar Duepaimvio was discovered and selected by the Inventor as a flowering plant from within the progeny of the stated cross-pollination in a controlled environment in Rheinberg, Germany in May, 2003.

Asexual reproduction of the new Ivy *Geranium* by vegetative terminal cuttings in a controlled environment in Rheinberg, Germany since July, 2003, has shown that the unique features of this new Ivy *Geranium* are stable and reproduced true to type in successive generations.

SUMMARY OF THE INVENTION

The cultivar Duepaimvio has not been observed under all possible environmental conditions. The phenotype may vary somewhat with variations in environment and cultural practices such as temperature, daylength and light intensity without, however, any variance in genotype.

The following traits have been repeatedly observed and are determined to be the unique characteristics of 'Duepaimvio'. These characteristics in combination distinguish 'Duepaimvio' as a new and distinct cultivar of Ivy *Geranium:*

1. Compact and outwardly spreading plant habit.
2. Freely basal branching habit.
3. Freely flowering habit.
4. Double red purple-colored flowers.
5. Good garden performance.

Plants of the new Ivy *Geranium* differ from plants of the female parent selection in the following characteristics:

1. Plants of the new Ivy *Geranium* are more vigorous than plants of the female parent selection.
2. Plants of the new Ivy *Geranium* and the female parent selection differ in flower color as plants of the female parent selection have orange-colored flowers.

Plants of the new Ivy *Geranium* differ from plants of the male parent selection in the following characteristics:

1. Plants of the new Ivy *Geranium* are more vigorous than plants of the male parent selection.
2. Plants of the new Ivy *Geranium* and the male parent selection differ in flower color as plants of the male parent selection have burgundy-colored flowers.

Plants of the new Ivy *Geranium* can be compared to plants of the *Pelargonium peltatum* cultivar Dueamelia, disclosed in U.S. Plant Pat. No. 15,751. In side-by-side comparison conducted in Rheinberg, Germany, plants of the new Ivy *Geranium* differed from plants of the cultivar Dueamelia in the following characteristics:

1. Plants of the new Ivy *Geranium* were more compact than plants of the cultivar Dueamelia.
2. Plants of the new Ivy *Geranium* and the cultivar Dueamelia differed in flower color as plants of the cultivar Dueamelia had more bluish purple-colored flowers.

BRIEF DESCRIPTION OF THE PHOTOGRAPH

The accompanying colored photograph illustrates the overall appearance of the new Ivy *Geranium*, showing the colors as true as it is reasonably possible to obtain in colored reproductions of this type. Colors in the photograph may differ slightly from the color values cited in the detailed botanical description which accurately describe the colors of the new Ivy *Geranium*. The photograph comprises a side perspective view of a typical flowering plant of 'Duepaimvio' grown in a container.

DETAILED BOTANICAL DESCRIPTION

The aforementioned photograph and following observations, measurements and values describe plants grown in Rheinberg, Germany in a glass-covered greenhouse during the summer and under conditions which closely approximate commercial production. During the production of the plants, day and night temperatures averaged 18° C. and light levels averaged 4,500 lux. Plants were about two months from planting when the photographs and the description were taken. Plants were pinched one time about three weeks after planting. In the detailed description, color references are made to The Royal Horticultural Society Colour Chart, 2001 Edition , except where general terms of ordinary dictionary significance are used.

Botanical classification: *Pelargonium peltatum* cultivar Duepaimvio.

Parentage:

*Female, or seed, parent.*—Proprietary selection of *Pelargonium peltatum* identified as code number S-01-06, not patented.

*Male or pollen parent.*—Proprietary selection of *Pelargonium peltatum* identified as code number E-01-02, not patented.

Propagation:

*Type.*—By vegetative terminal cuttings.

*Time to initiate roots, summer.*—About five days at temperatures of 20° C.

*Time to initiate roots, winter.*—About seven days at temperatures of 20° C.

*Time to produce a rooted young plant, summer.*—About three weeks at temperatures of 20° C.

*Time to produce a rooted young plant, winter.*—About four weeks at temperatures of 20° C.

*Root description.*—Fine, fibrous; white in color.

*Rooting habit.*—Freely branching.

Plant description:

*General appearance.*—Compact plant habit; outwardly spreading; uniformly rounded; densely foliated.

*Growth and branching habit.*—Moderately vigorous growth habit. Freely basal branching habit with about four lateral branches developing after the pinch.

*Plant height, to top of foliar plane.*—About 14 cm.

*Plant height, to top of umbels.*—About 19 cm.

*Plant width.*—About 12 cm.

*Lateral branches.*—Length: About 18 cm. Diameter: About 3 mm to 5 mm. Internode length: About 4.5 cm. Texture: Slightly pubescent. Strength: Strong. Color: 144A.

Foliage description:

*Arrangement.*—Alternate; simple.

*Length.*—About 6.5 cm.

*Width.*—About 7.3 cm.

*Shape.*—Reniform.

*Apex.*—Acute.

*Base.*—Cordate.

*Margin.*—Crenate.

*Venation pattern.*—Palmate.

*Texture, upper surface.*—Pubescent.

*Texture, lower surface.*—Smooth, glabrous.

*Color.*—Developing and fully expanded foliage, upper surface; 137A; venation, 144A. Developing and fully expanded foliage, lower surface; 144A; venation, 144A. Zonation pattern: Not observed. Petiole: Length: About 5.9 cm. Diameter: About 2 mm. Texture, upper and lower surfaces: Smooth, glabrous. Color, upper and lower surfaces: 144A.

Flower description:

*Flower arrangement.*—Double rotate flowers arranged in rounded hemispherical umbels arising from apical leaf axils. Umbels displayed above the foliage on strong peduncles. Flowers face upright to outward. Flowers persistent. Flowers not fragrant.

*Quantity of flowers.*—Freely flowering habit; about 15 flowers per umbel.

*Flowering season.*—Year-round under greenhouse conditions. In Germany, flowering is continuous from spring throughout the summer.

*Flower longevity.*—Individual flowers last about five to seven days on the plant.

*Umbel height.*—About 4.5 cm.

*Umbel diameter.*—About 7.5 cm.

*Flower diameter.*—About 4.5 cm.

*Flower depth* (*height*).—About 2 cm.

*Flower buds.*—Length: About 1.7 cm. Diameter: About 9.5 mm. Shape: Ovoid. Color: 66C.

*Petals.*—Quantity per flower: About five. Length: About 2.4 cm. Width: About 1.5 cm. Shape: Obovate. Apex: Rounded. Base: Attenuate. Margin: Sinuate. Aspect: Mostly flat. Texture, upper and lower surfaces: Smooth, glabrous. Color: When opening and fully opened, upper surface: 66A; venation similar to lamina. When opening and fully opened, lower surface: 66C; venation similar to lamina.

*Petaloids.*—Quantity per flower: About 15. Length: About 2.2 cm. Width: About 9 cm. Shape: Obovate. Apex: Rounded. Base: Attenuate. Margin: Sinuate. Texture, upper and lower surfaces: Smooth, glabrous. Color: When opening and fully opened, upper surface: 66A; venation similar to lamina. When opening and fully opened, lower surface: 66C; venation similar to lamina.

*Sepals.*—Quantity per flower: Five, arranged in a single whorl. Length: About 1.3 cm. Width: About 3 mm. Shape: Lanceolate. Apex: Apiculate. Base: Attenuate. Margin: Entire. Color, upper and lower surfaces: 144A.

*Peduncle* (*umbel stem*).—Length: About 12.8 cm. Diameter: About 2 mm to 4 mm. Strength: Moderately strong. Texture: Smooth, glabrous; leathery. Color: 144A.

*Pedicel* (*individual flower stem*).—Length: About 1.9 cm. Diameter: About 1 mm to 2 mm. Strength: Moderately strong. Texture: Pubescent. Color: 144A.

*Reproductive organs.*—Androecium: Stamen quantity per flower: About five. Anther length: About 3 mm. Anther shape: Oval. Anther color: 60A. Pollen amount: Moderate. Pollen color: 28A. Gynoecium: Pistil quantity per flower: One. Pistil length: About 1 cm. Stigma shape: Parted. Stigma size: About 2 mm. Stigma color: 66A. Style length: About 2 mm. Style color: 2D. Ovary color: Close to 145D.

*Seed/fruit.*—Seed and fruit development have not been observed.

Disease/pest resistance: Plants of the new Ivy *Geranium* have not been observed to be resistant to pathogens and pests common to Ivy *Geraniums*.

Garden performance: Plants of the new Ivy *Geranium* have been observed to tolerate rain, wind, and temperatures ranging from about 5° C. to about 40° C. and have demonstrated good garden performance.

It is claimed:

1. A new and distinct Ivy *Geranium* plant named 'Duepaimvio' as illustrated and described.

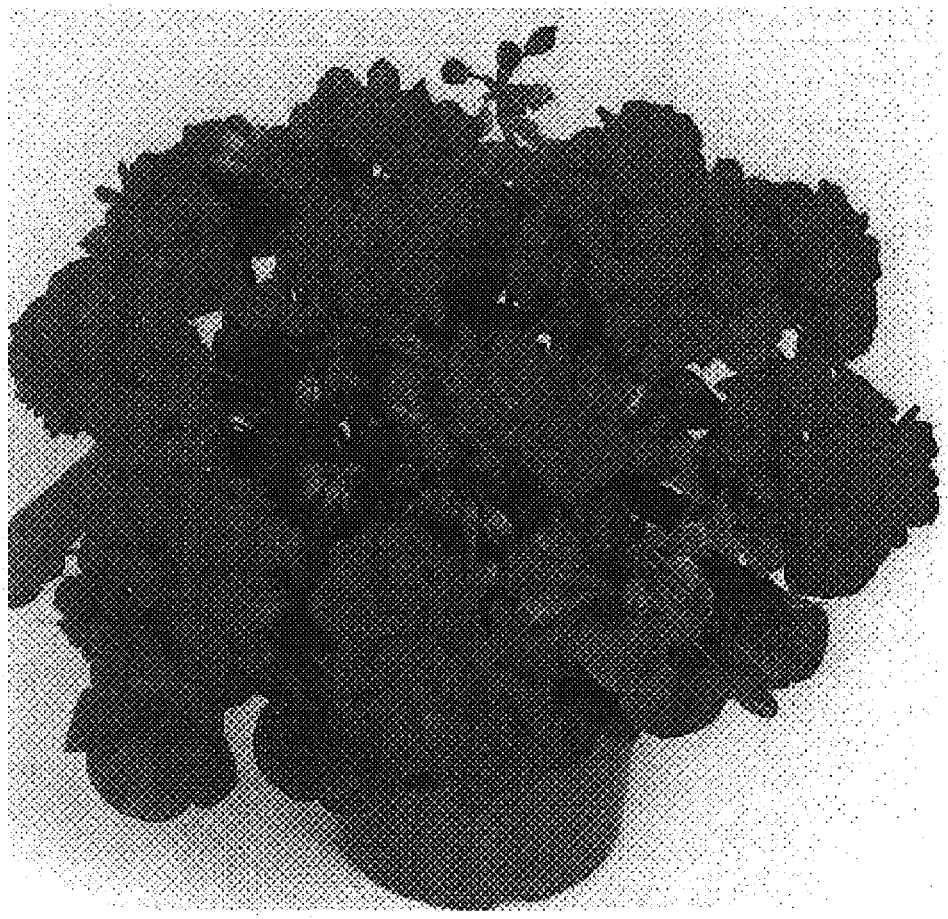

* * * * *